United States Patent [19]

De Scheerder et al.

[11] Patent Number: 5,578,149

[45] Date of Patent: Nov. 26, 1996

[54] RADIALLY EXPANDABLE STENT

[75] Inventors: Ivan De Scheerder, St. Martens Latem, Belgium; Joseph B. Horn, Niwot, Colo.

[73] Assignee: Global Therapeutics, Inc., Broomfield, Colo.

[21] Appl. No.: 456,087

[22] Filed: May 31, 1995

[51] Int. Cl.⁶ .............................. C21D 1/26; C22K 1/00
[52] U.S. Cl. .................. 148/563; 148/597; 148/598; 148/601; 623/901
[58] Field of Search ...................... 148/563, 596, 148/597, 598, 601, 542; 623/1, 901; 606/198

[56]     References Cited

U.S. PATENT DOCUMENTS

| | | | |
|---|---|---|---|
| 4,437,926 | 3/1984 | Barnabe | 148/542 |
| 4,733,665 | 3/1988 | Palmaz | 128/343 |
| 4,780,154 | 10/1988 | Mori et al. | 148/563 |
| 4,856,516 | 8/1989 | Hillstead | 128/343 |
| 4,886,062 | 12/1989 | Wiktor | 128/343 |
| 4,907,336 | 3/1990 | Gianturco | 29/515 |
| 5,041,126 | 8/1991 | Gianturco | 606/195 |
| 5,104,404 | 4/1992 | Wolff | 623/1 |
| 5,147,385 | 9/1992 | Beck et al. | 623/1 |
| 5,161,547 | 11/1992 | Tower | 128/898 |
| 5,217,483 | 6/1993 | Tower | 606/198 |
| 5,292,331 | 3/1994 | Boneau | 606/198 |
| 5,314,444 | 5/1994 | Gianturco | 606/195 |

FOREIGN PATENT DOCUMENTS 57-57837  4/1982  Japan .................... 148/596

*Primary Examiner*—George Wyszomierski
*Attorney, Agent, or Firm*—Sheridan Ross & McIntosh

[57]     ABSTRACT

The present invention is directed to an expandable stent for use in blood vessels. The length of the stent after expansion is substantially the same as the stent length before expansion. The stent is annealed at high temperatures to permit stent deformation at relatively low pressures to conform to the blood vessel shape and diameter.

7 Claims, 6 Drawing Sheets

RADIALLY EXPANDABLE STENT

FIELD OF THE INVENTION

The present invention is generally directed to a stent for use in blood vessels and specifically to a radially expandable stent for treating blood vessel constrictions.

BACKGROUND OF THE INVENTION

Balloon catheters and stents are normally used for treating blood vessel constrictions. Although balloon catheters are effective in removing constrictions, they can not only result in a dissection in the blood vessel (which causes the vessel to close and acute myocardial infarction to occur) but also increase the risk of another constriction occurring in the same portion of the blood vessel at a later time. Stents are commonly employed to overcome these problems. Stents are hollow tubes that are implanted inside of the blood vessel to "prop" the vessel open and prevent blood vessel constrictions and blockages.

Stents are available in a variety of configurations including self-expanding springs, mechanically actuated expandable devices, heat actuated expandable devices, and expandable sleeves. Of these various configurations, expandable sleeves are the most promising. Expandable sleeves are mounted on a collapsed catheter balloon and, after introduction into the vessel, expanded through the elastic limit of the metal by balloon expansion. The permanently deformed sleeve contacts and supports the interior wall of the blood vessel.

Though widely used, stents can have a number of limitations and can cause health complications. For example, stents can be limited in the radial strength of the stent (thereby limiting the amount of support provided to the interior wall of the blood vessel), in the maximum size of the stent (e.g., maximum stent diameter) after expansion (thereby limiting the stent to use in smaller diameter vessels), and/or in the minimum size of the stent profile that is to be inserted into the vessel (thereby limiting the stent to use in larger diameter vessels). Stents can also cause health complications after implantation including thrombogenic occlusion of the blood vessel (e.g., blood clots), restenoses (e.g., narrowing of the lumen of the blood vessel), and injury to the interior wall of the blood vessel wall during stent insertion, which can cause bleeding.

There is a need for a stent having a relatively high radial strength and therefore a relatively low risk of failure during use.

There is a further need for a stent having a broad range of sizes after expansion for use in blood vessels of a variety of sizes.

There is a further need for a stent having a low risk of injury to the blood vessel during insertion.

There is a further need for a stent that has a low risk of thrombosis after implantation in a blood vessel.

There is a further need for a stent that has a relatively low incidence of restenoses after implantation.

SUMMARY OF THE INVENTION

The present invention addresses these and other needs by providing a stent for use in a blood vessel that includes a plurality of concentric loops in a continuous wire along a length thereof. In a first state, the concentric loops have a first mean diameter along a first length of the wire. In a second state, the concentric loops have a second mean diameter, that is larger than the first mean diameter, along a second length of the wire. The second length is at least about 95% of the first length.

The present invention has a number of advantages relative to prior art stent devices. By way of example, the stent after expansion is substantially the same length as the stent before expansion. This feature permits doctors to select a stent which will extend the entire length of the diseased portion of the blood vessel after implantation. In contrast, existing stent devices have a length after implantation that is significantly less than the stent length before expansion. As a result, the stent length after expansion can be insufficient to extend the entire length of the diseased portion of the blood vessel which can cause restenoses and/or thrombosis. The stent also is substantially stable in the blood vessel after implantation. Unlike prior art stent devices, the stent will not move in response to blood flow. The stability of the stent in the blood vessel thereby reduces the risk of thrombosis relative to the prior art devices. Other advantages are set forth in the detailed discussion of the invention below.

DETAILED DESCRIPTION

Figure 1:
FIGS. 1–3 depict front, plan and side views of an embodiment of the present invention before expansion.
Figure 2:
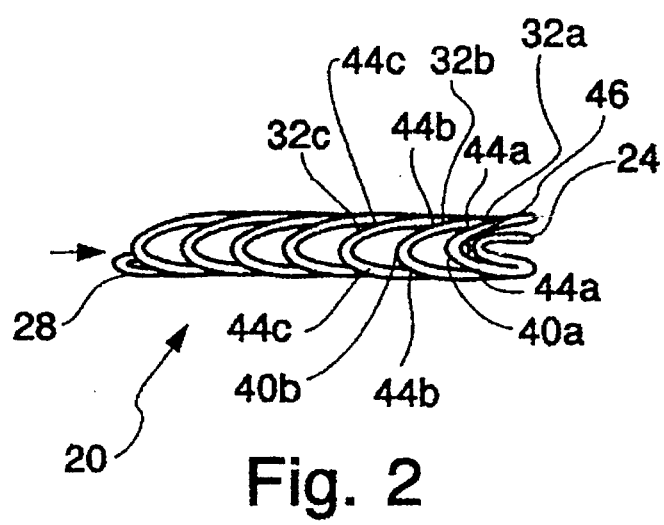
Figure 3:
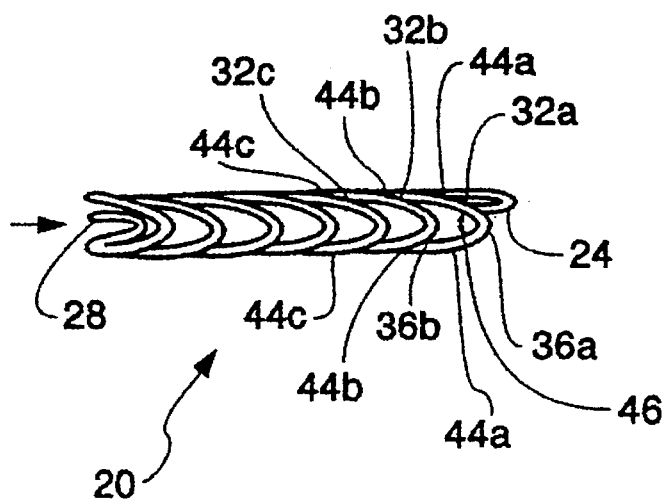
Figure 4:
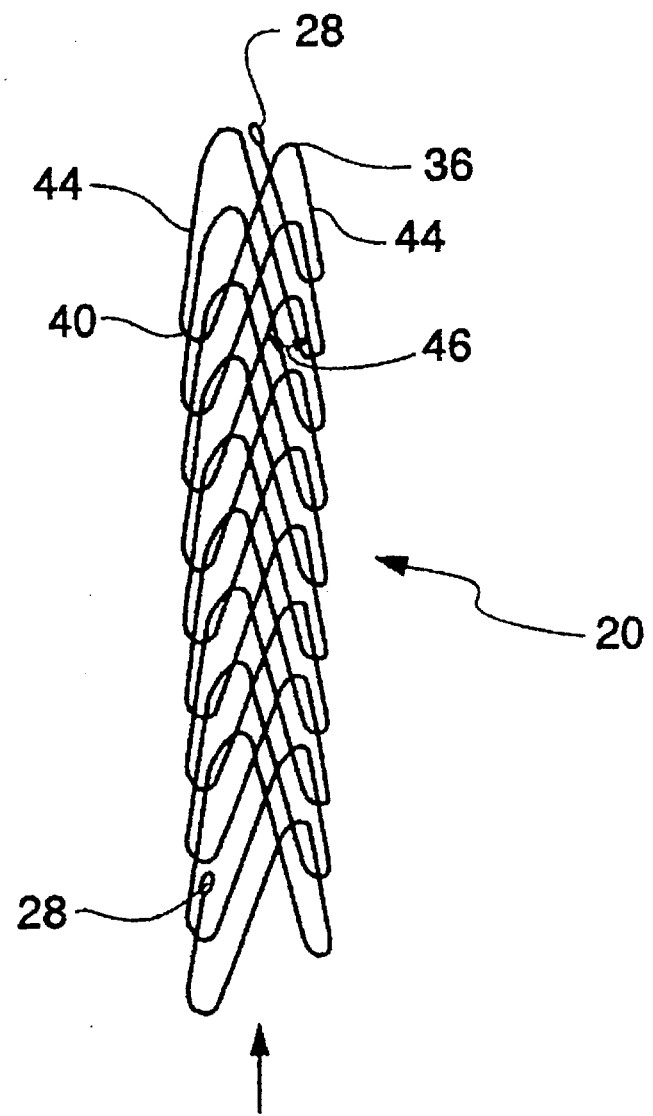
FIG. 4 is a perspective view of the embodiment.

Referring to FIGS. 1–4, a stent 20 according to the present invention is depicted before expansion (e.g., in a first state). The stent 20 has a substantially cylindrical profile and includes a distal end 24, a proximal end 28, and a plurality of concentric, interconnected support assemblies 32a,b, or loops, between the distal and proximal ends 24, 28. Each of the support assemblies 32 includes at least one, and preferably two, apex members 36a,b and connector members 40a,b, and at least four leg members 44a,b. The stent 20 is especially useful for treating blood vessel constrictions in humans and animals and complications arising during implementation of detection procedures for cardiac and vascular conditions.

The stent 20 is formed from a substantially continuous length of wire 50 and is free of connecting joints or welds between the distal and proximal ends 24,28. The absence of joints and welds in this portion of the stent 20 provides increased radial strength for the stent 20 relative to existing stent devices. The increased strength provides a significantly reduced incidence of stent failure during use.

The stent 20 has a length preferably ranging from about 8 mm to about 20 cm, and more preferably ranging from about 8 mm to about 10 cm, with the distribution of support assemblies 32 along the stent length ranging from about 3 to about 10 support assemblies/cm, and more preferably ranging from about 3.5 to about 6.5 support assemblies/cm, to yield a distance between adjacent support assemblies preferably ranging from about 0.5 to about 3.0 mm, and more preferably from about 1 to about 2.5 mm. As will be appreciated, if the distance between adjacent support assemblies 32a,b is too great, intimal flaps on the interior wall of the blood vessel can be trapped between the support assemblies and protrude into the blood vessel, thereby decreasing the luminal (e.g., cross-sectional area) area of the vessel.

Adjacent support assemblies 32a,b preferably do not contact one another except at the leg members 44. In other words, a leg member 44 of one support assembly 32a contacts the leg member of the adjacent support assembly 32b, and the leg member 44b of the support assembly 32b is connected to the leg member 44c of the adjacent support assembly 32c and so on to form the stent 20. The apex and connector members are independent of and preferably do not contact an adjacent support assembly 32.

The apex and connector members 36,40 are formed between adjacent leg members 44 and are slightly rounded with no sharp edges to avoid injury to the interior wall of the blood vessel or puncture of the catheter balloon during balloon dilation. At the apex and connector members, the leg members preferably form an angle 46 preferably ranging from about 10 to about 50 degrees and more preferably from about 40 to about 50 degrees. The angles 46 in the various apex and connector members 36,40 of all of the support assemblies 32 along the length of the stent are preferably substantially the same magnitude. The apex members 36 are preferably positioned downstream of the connector members 40.

The leg members 44 in the support assemblies are all of substantially the same length. Preferably, the length of the leg members 44 ranges from about 2 mm to about 3 mm.

The distal and proximal ends 24,28 are shaped to avoid injury to the blood vessel wall and/or puncture of the catheter balloon during insertion. Accordingly, the distal and proximal ends are generally bent inward or welded to provide a rounded profile. The proximal end 28 is preferably located upstream of the distal end 24.

The composition of the wire 50 in the stent 20 can be selected from a variety of suitable metals, such as stainless steel and platinum. For best results, stainless steel is employed. Stainless steel has a high radial strength and is relatively nonthrombogenic, especially stainless steel that has a low carbon content and was formed by vacuum molding techniques. The preferred stainless steel is a 316 LVM stainless steel wire.

The diameter of the wire 50 in the stent 20 preferably ranges from about 0.13 to about 0.24 mm. The wire diameter within this range selected for a specific application is based on the diameter of the blood vessel. For example, for blood vessel diameters ranging from about 2.5 to about 3.5 mm the wire diameter is preferably about 0.18 mm, from about 3.5 to about 6.0 mm the wire diameter is preferably about 0.20 mm, and from about 6.0 to about 10.0 mm the wire diameter is preferably about 0.24 mm.

Figure 5:
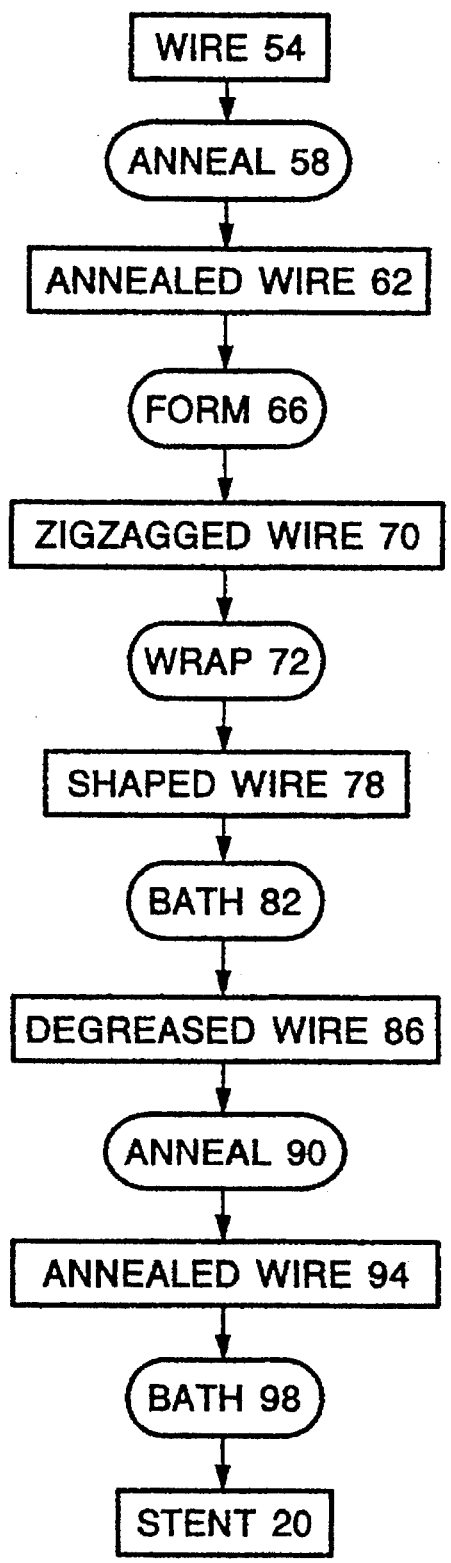
FIG. 5 is a flow schematic of the process to manufacture the embodiment of the present invention.

Referring to FIG. 5, the process for manufacturing the stent 20 will now be described. The process is an important aspect of the superior strength and shape adaptability of the stent relative to existing devices.

In the first step, the wire 54 is annealed 58 under a vacuum atmosphere at a temperature preferably ranging from about 900° to about 1200° C., more preferably from about 1000° to about 1100° C., and most preferably from about 1050° to about 1100° C. for a time preferably ranging from about 0.5 to about 2.0 hours and more preferably from about 0.75 to about 1.5 hours. The vacuum removes gases, such as oxygen, that can oxidize the wire surface. As will be appreciated, the annealing step can also be conducted in an inert atmosphere that is substantially free of gases such as oxygen.

Figure 6:
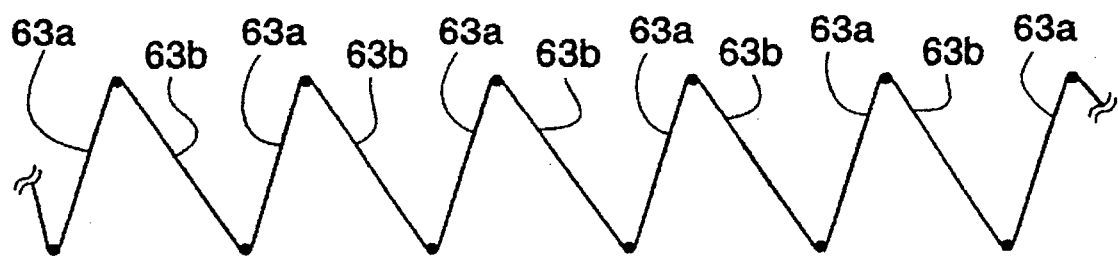
FIGS. 6–7 depict steps in manufacturing of the embodiment.

Referring to FIGS. 5–6, the annealed wire 62 is formed 66 on a die to the desired zigzag shape to form a zigzagged wire 70. The die can be a plurality of pins staggered such that a wire wrapped around the pins produces the zigzag shape in the wire. The high temperatures in the annealing step substantially eliminate the shape memory of the wire and thereby make it adapt readily to the zigzag shape. Preferably, there are from about 3.0 to about 6.0 cycles/cm in the zigzagged wire 70.

Figure 7:
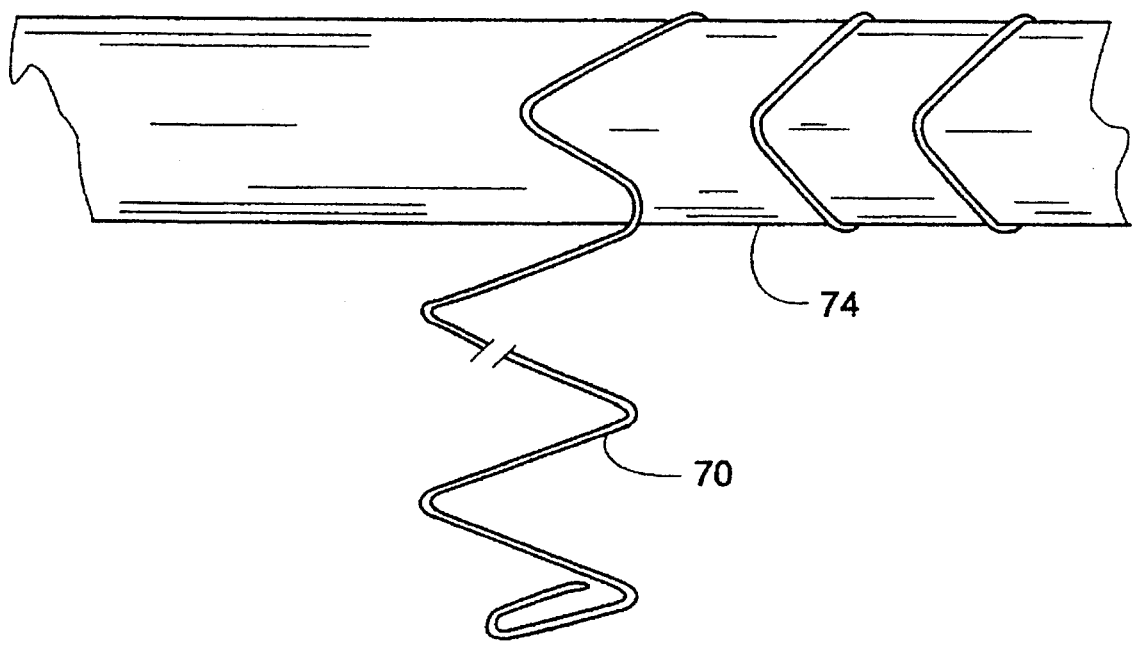

Referring to FIGS. 5 and 7, the zigzagged wire 70 is wrapped 72 around a dowel 74 in a spiral or helical fashion to form a shaped wire 78. The dowel 74 is preferably a 6F tubular device.

The shaped wire 78 is immersed in an ultrasonic bath 82 for approximately 30 minutes to yield a degreased wire 86. The bath contains a degreasing solution to remove grease, oils and other residues and particulates on the shaped wire 78.

The degreased wire 86 is then annealed 90 a second time under vacuum at the temperatures and times noted above to eliminate the shape memory of the wire and thereby make it adapt readily to the expanded shape in the blood vessel.

The annealed wire 94 is again immersed in an ultrasonic bath 98 to remove residue from the wire. The bath contains distilled water and is substantially free of degreasing solution. Distilled water permits the removal of materials from the wire that can cause complications after implantation in a patient.

After the above-described process, the stent of the present invention is relatively soft and flexible compared to many existing stent devices. The relative softness of the stent makes it deform plastically under low pressures to the desired shape. The flexibility of the stent enables it to be inserted in blood vessels having sharp bends and/or tortuous paths.

Figure 8:
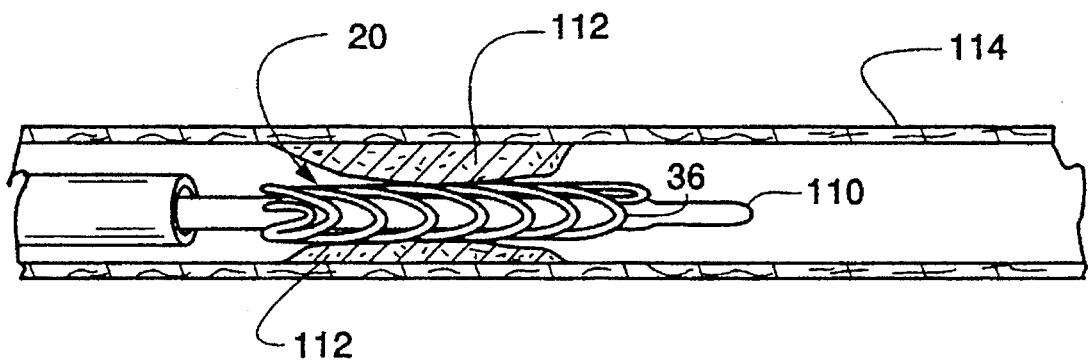
FIGS. 8–9 are various views depicting the implantation of the embodiment in a blood vessel.
Figure 9:
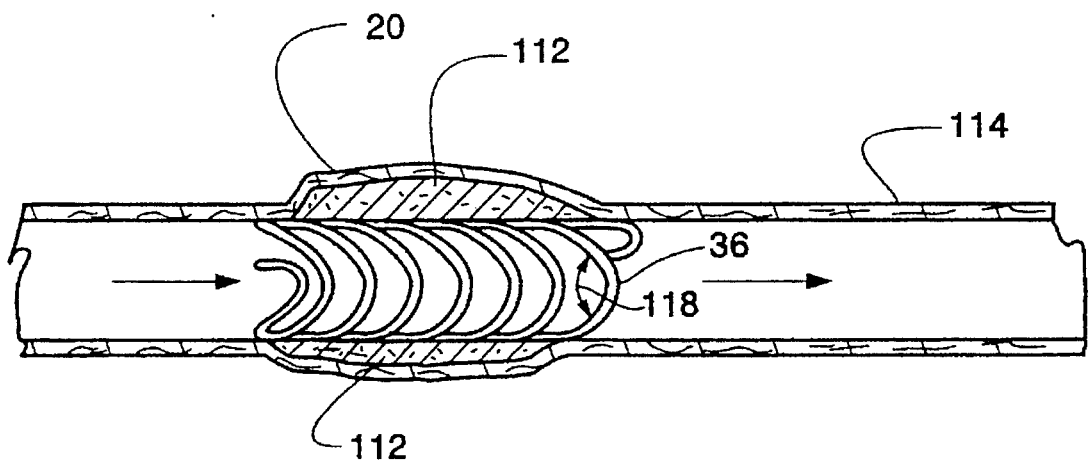

Referring to FIGS. 8–9, the implantation and operation of the stent will be described. The first step in implanting the stent is to select the proper stent diameter and length. The stent preferably has an outer diameter ranging from about 1.0 to about 4.0 mm and more preferably from about 1.0 to about 2.5 mm in size. The length of the stent is preferably sufficient to extend not only the length of the diseased portion of the blood vessel but also about 2 mm on either side of the diseased portion. Thus, the preferred stent length is the length of the diseased portion plus an additional 4 mm to overlap the adjacent healthy portions of the vessel.

As shown in FIG. 8, the stent 20 is placed over the deflated catheter balloon 110 and compressed to embed the stent 20 into the balloon 110 before insertion into the blood vessel 114. The substantially cylindrical profile of the stent 20 on the catheter balloon 110 is relatively small and permits the use of a smaller catheter (e.g., a 6 french guide catheter as opposed to the 8 french guide catheter used in existing stent devices) and provides the ability to pass sharp bends or corners and negotiate tortuous paths in the blood vessel 114.

After insertion of the catheter balloon 110 and stent 20 into the blood vessel 114, the balloon and stent are moved to the desired location in the blood vessel to dislodge plaque 112 and open up the blood vessel 114. The position of the balloon and stent in the vessel are determined by fluoroscopic or other suitable means.

When the balloon 110 and stent 20 are in the desired position, the balloon 110 is inflated to a pressure preferably ranging from about 5 to about 14 atms, more preferably ranging from about 6 to about 10 atms, and most preferably from about 7 to about 8 atms. As the balloon 110 expands, the stent plastically deforms into a second state. The stent diameter is larger than the stent diameter in the first state with the lengths of the original (e.g., unexpanded) and expanded stent being substantially the same. The stent length after expansion preferably ms at least about 95%, more preferably at least about 98%, and most preferably at least about 99% of the original (unexpanded) stent length.

The substantial maintenance of the original stent length after expansion results from the unique manner in which the stent changes shape. The angle 46 in each apex and connector member increases in magnitude to form a second angle 118 and thereby provides the increased stent diameter without a shortening of the stent. The second angle 118 in the apex and connector members preferably ranges from about 50 to about 80 degrees and more preferably from about 60 to about 75 degrees.

The stent diameter after expansion is determined by the diameter of the catheter balloon used for deploying the stent. It is desirable to use a catheter balloon having a diameter sufficient to provide an outer stent diameter that is about 0.25 to about 0.50 larger than the interior diameter of the blood vessel. The outer diameter of the stent at full expansion preferably ranges from about 2.75 to about 10.50 mm and more preferably ranges from about 2.75 to about 5.50 mm. Preferably, the outer diameter of the expanded stent ranges from about 150 to about 300% of the original (unexpanded) stent outer diameter.

The stent of the present invention can expand to a much greater degree than existing stent devices. Accordingly, a single size of stent is able to be expanded to treat a broad range of blood vessel sizes. This feature provides ease of use by physicians at a reduced cost (due to a reduced stent inventory). By way of example, a single stent can produce a blood vessel diameter ranging from about 2.5 to about 3.5 mm. Stents 20 can be used for blood vessels having diameters preferably ranging from about 2.5 to about 10.0 mm and more preferably from about 2.5 mm to about 5.0 mm.

After the constriction formed by the plaque 112 is removed and the stent properly expanded, the catheter balloon 110 is deflated and removed from the stent 20 and blood vessel 114.

Referring to FIG. 9, the expanded stent after removal of the catheter balloon 110 maintains its shape and diameter in the blood vessel 114 and experiences little or no movement in the blood vessel 114. Movement of the stent in the blood vessel can result in thrombosis, which is a problem for many existing stent devices. The stability of the stent of the present invention is due to the softness and flexibility of the metal wire in the stent coupled with the stent design. The stent softness and flexibility and zigzag configuration permit the stent to plastically deform to substantially match the shape of the blood vessel and thereby inhibit movement of the stent in the vessel. As will be appreciated, blood vessels normally have a diameter and shape that fluctuate along a given length of the blood vessel. Accordingly, along the length of the stent the angles 118 in each support assembly 32 can have differing magnitudes depending upon the diameter and shape of the blood vessel.

To further reduce the thrombogenicity of the stent, the stent can have a coating of an anti-coagulant. In most applications, the stent has an acceptable degree of thrombogenicity without the use of such a coating.

EXAMPLE

The stent was used in experimental trials to determine its effectiveness in actual use. It was discovered that the stent could be placed very far distally and navigate sharp bends in the blood vessel.

The stent was also found to be reliable. No problems were encountered with the proper placement of the stent and balloon rupture. The placement of the stent did not give rise to problems associated with the withdrawal of the balloon. These problems are frequent with existing devices used under the same experimental conditions.

Angiographic controls after placement of the stents showed a well opened vascular lumen without intravascular brightening and signs of distal or proximal dissection. It also appeared that the side branches at the level of the vessel segment bearing the stent were intact.

Follow-up investigations after 7 days showed that the entire stent remained open without evolution of thrombotic developments, though no anticoagulant therapy was administered in the study.

Follow-up investigations after 6 weeks showed that no substantial reactive neointimal growth was induced by the stent.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the appended claims.

What is claimed is:

1. A method for manufacturing a stent and for deploying said stent having a length in a vessel in a body, comprising:

providing a wire that is to be subject to annealing at two different times after said providing step;

first annealing said wire at a temperature ranging from about 900° to about 1200° C., wherein said first annealing step substantially eliminates any shape memory of said wire;

changing the shape of said wire into that of a stent having concentric loops;

second annealing, after said changing step, said stent at a temperature ranging from about 900° to about 1200° C., wherein said second annealing step substantially eliminates any shape memory of said stent and renders said stent able to adapt readily to the shape of said vessel;

placing said stent within an interior of the body vessel;

permitting said stent to conform to the shape of the interior of the body vessel.

2. The method as claimed in claim 1, wherein said temperature in at least one of said first and second annealing steps ranges from about 1000° to about 1100° C.

3. The method as claimed in claim 1, wherein said temperature in at least one of said first and second annealing steps ranges from about 1050° to about 1100° C.

4. A method, as claimed in claim 1, wherein:

said changing step includes creating a zigzag wire before said wire is changed into a plurality of concentric loops.

5. A method, as claimed in claim 1, wherein:

said first annealing step is performed in an atmosphere that is substantially free of oxygen to inhibit oxidation of said wire.

6. A method, as claimed in claim 1, wherein:

said second annealing step is performed in an atmosphere that is substantially free of oxygen to inhibit oxidation of said stent.

7. A method, as claimed in claim 1, wherein:

said permitting step includes expanding a diameter of said stent after placement in the interior of the body vessel while the length of said stent remains substantially the same.

* * * * *